US009723992B2

(12) United States Patent
Senechal et al.

(10) Patent No.: US 9,723,992 B2
(45) Date of Patent: Aug. 8, 2017

(54) MENTAL STATE ANALYSIS USING BLINK RATE

(71) Applicant: Affectiva, Inc., Waltham, MA (US)

(72) Inventors: Thibaud Senechal, Cambridge, MA (US); Rana el Kaliouby, Boston, MA (US); Niels Haering, Reston, VA (US)

(73) Assignee: Affectiva, Inc., Boston, MA (US)

( * ) Notice: Subject to any disclaimer, the term of this patent is extended or adjusted under 35 U.S.C. 154(b) by 0 days.

(21) Appl. No.: 14/214,918

(22) Filed: Mar. 15, 2014

(65) Prior Publication Data

US 2014/0200417 A1     Jul. 17, 2014

Related U.S. Application Data

(63) Continuation-in-part of application No. 13/153,745, filed on Jun. 6, 2011.
(Continued)

(51) Int. Cl.
*G06K 9/00* (2006.01)
*A61B 5/00* (2006.01)
(Continued)

(52) U.S. Cl.
CPC ........ *A61B 5/0077* (2013.01); *A61B 5/02405* (2013.01); *A61B 5/08* (2013.01);
(Continued)

(58) Field of Classification Search
CPC .......... G06K 9/00275; G06K 9/00281; G06K 9/0028; G06K 9/00295; G06K 9/00302;
(Continued)

(56) References Cited

U.S. PATENT DOCUMENTS 3,034,500 A     5/1962 Backster, Jr.
3,548,806 A     12/1970 Fisher
(Continued)

FOREIGN PATENT DOCUMENTS

JP           08115367    7/1996
KR    10-2005-0021759 A   3/2005
(Continued)

OTHER PUBLICATIONS

Rana Ayman El Kaliouby, Mind-reading machines: automated inference of complex mental states, Jul. 2005, of Cambridge, Cambridge, United Kingdom University.
(Continued)

*Primary Examiner* — Wesley Tucker
(74) *Attorney, Agent, or Firm* — Adams Intellex, PLC

(57) ABSTRACT

Mental state analysis is performed by obtaining video of an individual as the individual interacts with a computer, either by performing various operations or by consuming a media presentation. The video is analyzed to determine eye-blink information on the individual, such as eye-blink rate or eye-blink duration. A mental state of the individual is then inferred based on the eye blink information. The blink-rate information and associated mental states can be used to modify an advertisement, a media presentation, or a digital game.

38 Claims, 7 Drawing Sheets

Related U.S. Application Data

(60) Provisional application No. 61/789,038, filed on Mar. 15, 2013, provisional application No. 61/793,761, filed on Mar. 15, 2013, provisional application No. 61/790,461, filed on Mar. 15, 2013, provisional application No. 61/798,731, filed on Mar. 15, 2013, provisional application No. 61/844,478, filed on Jul. 10, 2013, provisional application No. 61/916,190, filed on Dec. 14, 2013, provisional application No. 61/924,252, filed on Jan. 7, 2014, provisional application No. 61/927,481, filed on Jan. 15, 2014, provisional application No. 61/352,166, filed on Jun. 7, 2010, provisional application No. 61/388,002, filed on Sep. 30, 2010, provisional application No. 61/414,451, filed on Nov. 17, 2010, provisional application No. 61/439,913, filed on Feb. 6, 2011, provisional application No. 61/447,089, filed on Feb. 27, 2011, provisional application No. 61/447,464, filed on Feb. 28, 2011, provisional application No. 61/467,209, filed on Mar. 24, 2011.

(51) Int. Cl.
   *A61B 5/024* (2006.01)
   *A61B 5/08* (2006.01)
   *A61B 5/16* (2006.01)
   *G06F 19/00* (2011.01)
   *A61B 5/0205* (2006.01)
   *G06Q 30/02* (2012.01)
   *A61B 5/11* (2006.01)

(52) U.S. Cl.
   CPC .......... *A61B 5/165* (2013.01); *G06F 19/3418* (2013.01); *G06F 19/3481* (2013.01); *A61B 5/02055* (2013.01); *A61B 5/1114* (2013.01); *A61B 5/441* (2013.01); *G06F 19/345* (2013.01); *G06Q 30/0271* (2013.01)

(58) Field of Classification Search
   CPC .......... G06K 9/00308; G06K 9/00315; G06K 9/00335; G06K 9/00342; G06K 9/00348; G06K 9/00355; G06K 9/362; G06K 9/241; H04N 21/44218
   USPC ....................................................... 382/118
   See application file for complete search history.

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | Maclean |
| 5,507,291 A | 4/1996 | Stirbl et al. |
| 5,572,596 A | 11/1996 | Wildes et al. |
| 5,619,571 A | 4/1997 | Sandstrom et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,741,217 A | 4/1998 | Gero |
| 5,760,917 A | 6/1998 | Sheridan |
| 5,762,611 A | 6/1998 | Lewis et al. |
| 5,772,591 A | 6/1998 | Cram |
| 5,774,591 A | 6/1998 | Black et al. |
| 5,802,220 A | 9/1998 | Black et al. |
| 5,825,355 A | 10/1998 | Palmer et al. |
| 5,867,587 A * | 2/1999 | Aboutalib et al. ............ 382/117 |
| 5,886,683 A | 3/1999 | Tognazzini et al. |
| 5,898,423 A | 4/1999 | Tognazzini et al. |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,099,319 A | 8/2000 | Zaltman et al. |
| 6,134,644 A | 10/2000 | Mayuzumi et al. |
| 6,182,098 B1 | 1/2001 | Selker |
| 6,185,534 B1 | 2/2001 | Breese et al. |
| 6,195,651 B1 | 2/2001 | Handel et al. |
| 6,212,502 B1 | 4/2001 | Ball et al. |
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |
| 6,351,273 B1 | 2/2002 | Lemelson et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |
| 6,606,102 B1 | 8/2003 | Odom |
| 6,629,104 B1 | 9/2003 | Parulski et al. |
| 6,792,458 B1 | 9/2004 | Muret et al. |
| 6,847,376 B2 | 1/2005 | Engeldrum et al. |
| 7,013,478 B1 | 3/2006 | Hendricks et al. |
| 7,113,916 B1 | 9/2006 | Hill |
| 7,120,880 B1 | 10/2006 | Dryer et al. |
| 7,197,459 B1 | 3/2007 | Harinarayan et al. |
| 7,233,684 B2 | 6/2007 | Fedorovskaya et al. |
| 7,246,081 B2 | 7/2007 | Hill |
| 7,263,474 B2 | 8/2007 | Fables et al. |
| 7,266,582 B2 | 9/2007 | Stelting |
| 7,307,636 B2 | 12/2007 | Matraszek et al. |
| 7,327,505 B2 | 2/2008 | Fedorovskaya et al. |
| 7,350,138 B1 | 3/2008 | Swaminathan et al. |
| 7,353,399 B2 | 4/2008 | Ooi et al. |
| 7,355,627 B2 | 4/2008 | Yamazaki et al. |
| 7,428,318 B1 | 9/2008 | Madsen et al. |
| 7,496,622 B2 | 2/2009 | Brown et al. |
| 7,549,161 B2 | 6/2009 | Poo et al. |
| 7,551,755 B1 | 6/2009 | Steinberg et al. |
| 7,555,148 B1 | 6/2009 | Steinberg et al. |
| 7,558,408 B1 | 7/2009 | Steinberg et al. |
| 7,564,994 B1 | 7/2009 | Steinberg et al. |
| 7,573,439 B2 | 8/2009 | Lau et al. |
| 7,580,512 B2 | 8/2009 | Batni et al. |
| 7,584,435 B2 | 9/2009 | Bailey et al. |
| 7,587,068 B1 | 9/2009 | Steinberg et al. |
| 7,610,289 B2 | 10/2009 | Muret et al. |
| 7,620,934 B2 | 11/2009 | Falter et al. |
| 7,644,375 B1 | 1/2010 | Anderson et al. |
| 7,676,574 B2 | 3/2010 | Glommen et al. |
| 7,747,801 B2 | 6/2010 | Han et al. |
| 7,826,657 B2 | 11/2010 | Zhang et al. |
| 7,830,570 B2 | 11/2010 | Morita et al. |
| 7,881,493 B1 | 2/2011 | Edwards et al. |
| 7,921,036 B1 | 4/2011 | Sharma |
| 8,010,458 B2 | 8/2011 | Galbreath et al. |
| 8,401,248 B1 | 3/2013 | Moon et al. |
| 8,600,120 B2 | 12/2013 | Gonion et al. |
| 2001/0033286 A1 | 10/2001 | Stokes et al. |

(56) References Cited

U.S. PATENT DOCUMENTS

| | | |
|---|---|---|
| 2001/0041021 A1 | 11/2001 | Boyle et al. |
| 2002/0007249 A1 | 1/2002 | Cranley |
| 2002/0030665 A1 | 3/2002 | Ano |
| 2002/0042557 A1 | 4/2002 | Bensen et al. |
| 2002/0054174 A1 | 5/2002 | Abbott et al. |
| 2002/0084902 A1 | 7/2002 | Zadrozny et al. |
| 2002/0105427 A1* | 8/2002 | Hamamoto et al. ......... 340/576 |
| 2002/0171551 A1 | 11/2002 | Eshelman |
| 2002/0182574 A1 | 12/2002 | Freer |
| 2003/0035567 A1 | 2/2003 | Chang et al. |
| 2003/0037041 A1 | 2/2003 | Hertz |
| 2003/0060728 A1 | 3/2003 | Mandigo |
| 2003/0078513 A1 | 4/2003 | Marshall |
| 2003/0093784 A1 | 5/2003 | Dimitrova et al. |
| 2003/0169907 A1* | 9/2003 | Edwards ............ G06K 9/00248 382/118 |
| 2003/0191682 A1 | 10/2003 | Shepard et al. |
| 2003/0191816 A1 | 10/2003 | Landress et al. |
| 2004/0181457 A1 | 9/2004 | Biebesheimer et al. |
| 2005/0187437 A1 | 8/2005 | Matsugu |
| 2005/0283055 A1 | 12/2005 | Shirai et al. |
| 2005/0289582 A1 | 12/2005 | Tavares et al. |
| 2006/0019224 A1 | 1/2006 | Behar et al. |
| 2006/0115157 A1 | 6/2006 | Mori |
| 2006/0143647 A1 | 6/2006 | Bill |
| 2006/0235753 A1 | 10/2006 | Kameyama |
| 2007/0167689 A1 | 7/2007 | Ramadas et al. |
| 2007/0239787 A1 | 10/2007 | Cunningham et al. |
| 2007/0255831 A1 | 11/2007 | Hayashi et al. |
| 2007/0265507 A1* | 11/2007 | de Lemos ............ A61B 3/113 600/300 |
| 2007/0299964 A1 | 12/2007 | Wong et al. |
| 2008/0091512 A1* | 4/2008 | Marci et al. .................... 705/10 |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0184170 A1 | 7/2008 | Periyalwar |
| 2008/0208015 A1 | 8/2008 | Morris et al. |
| 2008/0218472 A1* | 9/2008 | Breen et al. .................. 345/156 |
| 2008/0221472 A1 | 9/2008 | Lee et al. |
| 2008/0287821 A1 | 11/2008 | Jung et al. |
| 2009/0006206 A1 | 1/2009 | Groe et al. |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0133048 A1 | 5/2009 | Gibbs et al. |
| 2009/0147080 A1* | 6/2009 | Inada .............................. 348/77 |
| 2009/0150919 A1 | 6/2009 | Lee et al. |
| 2009/0210290 A1 | 8/2009 | Elliott et al. |
| 2009/0217315 A1 | 8/2009 | Malik et al. |
| 2009/0271417 A1 | 10/2009 | Toebes et al. |
| 2009/0299840 A1 | 12/2009 | Smith |
| 2010/0070523 A1 | 3/2010 | Delgo et al. |
| 2010/0099955 A1 | 4/2010 | Thomas et al. |
| 2010/0266213 A1 | 10/2010 | Hill |
| 2010/0274847 A1 | 10/2010 | Anderson |
| 2011/0092780 A1 | 4/2011 | Zhang et al. |
| 2011/0102553 A1* | 5/2011 | Corcoran et al. ............... 348/50 |
| 2011/0126226 A1 | 5/2011 | Makhlouf |
| 2011/0134026 A1 | 6/2011 | Kang et al. |
| 2011/0143728 A1 | 6/2011 | Holopainen et al. |
| 2011/0196855 A1 | 8/2011 | Wable et al. |
| 2011/0231240 A1 | 9/2011 | Schoen et al. |
| 2011/0251493 A1 | 10/2011 | Poh et al. |
| 2011/0263946 A1 | 10/2011 | el Kaliouby et al. |
| 2012/0229248 A1* | 9/2012 | Parshionikar et al. ........ 340/3.1 |
| 2012/0293548 A1 | 11/2012 | Perez et al. |
| 2012/0304206 A1 | 11/2012 | Roberts et al. |
| 2013/0215390 A1* | 8/2013 | Johns ..................... A61B 3/113 351/209 |
| 2014/0192325 A1* | 7/2014 | Klin ........................ A61B 5/16 351/209 |
| 2014/0198196 A1* | 7/2014 | Howard ............. G06K 9/00281 348/78 |

FOREIGN PATENT DOCUMENTS

| | | |
|---|---|---|
| KR | 10-2008-0016303 A | 2/2008 |
| KR | 1020100048688 A | 5/2010 |
| KR | 100964325 B1 | 6/2010 |
| KR | 1020100094897 A | 8/2010 |
| WO | WO 2011/045422 A1 | 4/2011 |

OTHER PUBLICATIONS

International Search Report dated Nov. 14, 2011 for PCT/US2011/39282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

* cited by examiner

MENTAL STATE ANALYSIS USING BLINK RATE

RELATED APPLICATIONS

This application claims the benefit of U.S. provisional patent applications "Mental State Analysis Using Blink Rate" Ser. No. 61/789,038, filed Mar. 15, 2013, "Mental State Analysis Using Heart Rate Collection Based on Video Imagery" Ser. No. 61/793,761, filed Mar. 15, 2013, "Mental State Data Tagging for Data Collected from Multiple Sources" Ser. No. 61/790,461, filed Mar. 15, 2013, "Mental State Well Being Monitoring" Ser. No. 61/798,731, filed Mar. 15, 2013, "Personal Emotional Profile Generation" Ser. No. 61/844,478, filed Jul. 10, 2013, "Heart Rate Variability Evaluation for Mental State Analysis" Ser. No. 61/916,190, filed Dec. 14, 2013, "Mental State Analysis Using an Application Programming Interface" Ser. No. 61/924,252, filed Jan. 7, 2014, and "Mental State Analysis for Norm Generation" Ser. No. 61/927,481, filed Jan. 15, 2014. This application is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011. The foregoing applications are each hereby incorporated by reference in their entirety.

FIELD OF ART

This application relates generally to analysis of mental states and more particularly to mental state analysis using eye blink rates.

BACKGROUND

An individual's mental state may manifest itself in many different ways. Some of these manifestations are externally detectable, such as facial expressions, heart rate, sweating, and changes to respiration and blood pressure. A person's mental state may be impacted by many types of external stimuli. One increasingly common external stimulus is interaction with a computer. People spend ever-larger amounts of time interacting with computers, and consume a vast amount of computer-delivered media. This interaction may be for many different reasons, such as a desire for educational content, entertainment, social media interaction, document creation, and gaming, to name a few.

In some cases the human-computer interaction can take the form of a person performing a task using the computer and a software tool running on the computer. Examples of this can include creating a document, editing a video, or doing one or more of the other activities enabled by modern computers. The person might find certain activities interesting or even exciting to perform, and might be surprised at how easy it is to accomplish the activities. The person can become excited, happy, or content as they perform those activities. On the other hand, the person might find some activities difficult to perform, and might become frustrated or even angry with the computer, even though the computer is oblivious to his or her emotions. In other cases of human-computer interaction, the person might be consuming content or media, such as news, pictures, music or video. A person's mental state can prove useful in determining whether the person enjoys the media.

In some cases, users can be surveyed to try to determine their mental state in reaction to a stimulus, such as the previously mentioned human-computer interaction. Survey results are often unreliable because the surveys are often done well after the activity was performed. Additionally survey participation rates may be low, and people might not provide accurate and honest answers to the survey. In another manner of determining mental state reactions, people can self-rate media to communicate personal preferences by entering a specific number of stars corresponding to a level of like or dislike. These types of subjective evaluations are, in many cases, neither a reliable nor practical way to evaluate personal response to media. Recommendations based on such methods are imprecise, subjective, unreliable, and are often further subject to problems related to the small number of individuals willing to participate in such evaluations.

SUMMARY

A mental state analysis includes obtaining video of an individual as the individual is interacting with a computer, either by performing various operations or by consuming a media presentation. The video is then analyzed to determine eye blink information on the individual, such as eye blink rate and/or eye blink duration. A mental state of the individual is then inferred based on the eye blink information. A computer-implemented method for mental state analysis is disclosed comprising obtaining video of an individual; analyzing the video to detect a blink event; and inferring mental states of the individual based on the blink event.

The method may include evaluating blink duration for the blink event. The method may further comprise using the blink event and one or more other blink events to determine blink-rate information. The method can further include aggregating the blink-rate information for the individual with blink-rate information for a plurality of other people. The method may include comprise determining a classifier for a blink. The inferring of mental states may include one or more of attention, concentration, boredom, or fatigue.

In embodiments, a computer program product embodied in a non-transitory computer readable medium for mental state analysis may comprise: code for obtaining video of an individual; code for analyzing the video to determine a blink event; and code for inferring mental states of the individual based on the blink event. In some embodiments, a computer system for mental state analysis may comprise: a memory which stores instructions; one or more processors attached to the memory wherein the one or more processors, when executing the instructions which are stored, are configured to: obtain video of an individual; analyze the video to determine a blink event; and infer mental states of the individual based on the blink event. In embodiments, a computer-implemented method for mental state analysis may comprise: receiving eye blink-rate information obtained from video of an individual; and inferring mental states of the individual based on the eye blink-rate information. In some embodiments, a computer-implemented method for mental state analysis may comprise: capturing video of an individual; analyzing the video to determine eye blink-rate information; and sending the eye blink-rate information for inferring mental states. In embodiments, a computer-implemented method for mental state analysis may comprise: receiving eye blink-rate information based on video of an individual; receiving mental state information inferred from the eye blink-rate information; and rendering one or more of the eye blink-rate information and the mental state information which was inferred.

Various features, aspects, and advantages of various embodiments will become more apparent from the following further description.

BRIEF DESCRIPTION OF THE DRAWINGS

The following detailed description of certain embodiments may be understood by reference to the following figures wherein.

DETAILED DESCRIPTION

Figure 1:
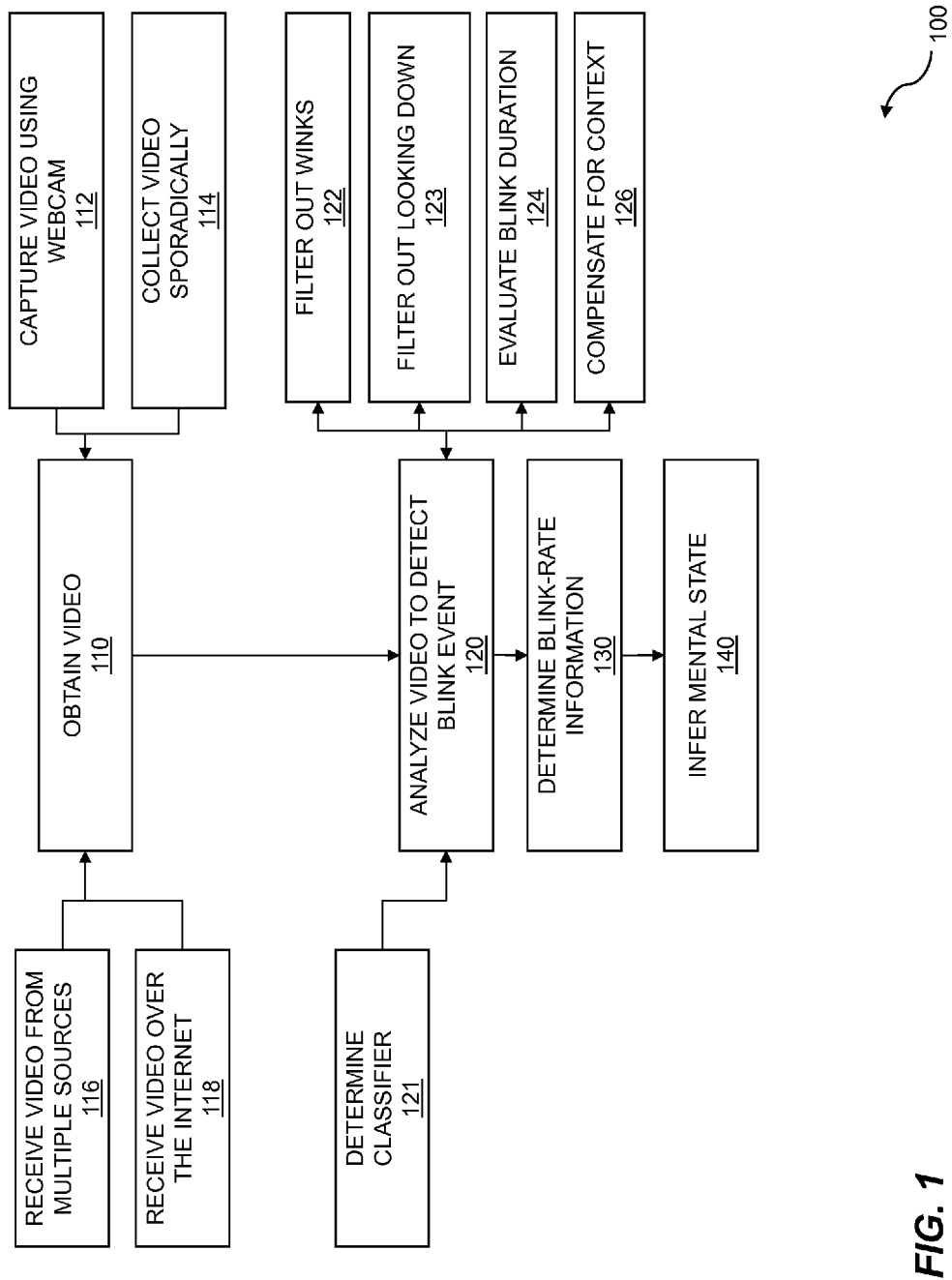
FIG. 1 is a flow diagram for blink rate and mental state analysis.

Many manifestations of an individual's mental state can be observed through the individual's actions and/or behavior. Such external manifestations that can be related to mental state include facial movements such as smiling, frowning, grimacing, and laughing. One additional facial movement that can be related to an individual's mental state is eye blinking That is, the rate at which an individual blinks his or her eyes and/or the duration of a single eye blink can be related to an individual's mental state.

An individual's mental state can be impacted by his or her interaction with a computer. Understanding the individual's mental state during such interactions can be valuable for a variety of reasons, such as improving the program that the individual is using, rating a media presentation, or optimizing an advertisement. Traditional methods of monitoring an individual's mental state often do not provide an effective way to monitor the individual's mental state during his or her interaction with a computer, for a variety of reasons. For example, surveys or rating systems are prone to non-participation and inaccurate reporting, and even though physiological information can in some instances provide an accurate measure of mental state, traditional physiological monitoring devices are intrusive and not available at most computer workstations.

In contrast, a webcam is able to unobtrusively monitor an individual as they interact with the computer. Many computer systems today already include a webcam, and for systems that do not already have one, a webcam can be easily and inexpensively added to nearly any modern computer workstation. An individual can interact with a computer to view a media presentation or to perform some type of task on the computer while being monitored by a webcam. In some embodiments, some other type of image capture device, for example, a security camera or a camera on a mobile device such as a tablet or a phone, is used to monitor the individual in place of, or in addition to, the webcam. The video from the webcam is then analyzed to determine eye blink information. The eye blink information can include eye-blink rate, eye-blink duration, time between blinks, and/or other information related to one or more eye blinks by the individual being monitored.

Once the eye blink information is determined, the eye blink information can be correlated with context, for example, the activity being performed by the user, demographic information about the user such as the user's age and/or gender, the time of day, the brightness of the screen and/or environment, or other contextual information. In some embodiments, the eye-blink information is compensated, or adjusted, based on the context. The eye blink information can then be used to infer the mental state of the individual, which is correlated to context in some embodiments. The mental state can be used to modify the activity being performed, a game being played, a choice of advertisement to be displayed, a media presentation, or some other activity. In some embodiments, an output is rendered to display the mental states and/or eye blink information, which can be correlated with the context, such as the timeline of a media presentation.

FIG. 1 is a flow diagram for blink rate and mental state analysis. The flow 100 describes a computer-implemented method for mental state analysis and begins by obtaining video 110 of an individual. In some embodiments, the video is captured using a webcam 112. The video can be captured continuously or can be captured sporadically 114 due to the individual moving outside of the camera's field of view, limited storage space, or a lack of interest in an individual's mental state during a particular time period, among other reasons for a cessation of recording. The video can also be captured from multiple sources 116, for example, by additional cameras such as cameras in a mobile device, security cameras, or other cameras. In some embodiments, the video is received over the internet 118 from another computer.

The flow 100 further comprises analyzing the video 120 to detect a blink event. A blink event can start with an eye being open but starting to close. The blink event can conclude with the eye opening or going back to its normal state. The analysis of the video can include detecting on each frame of the video, or portion of the video, whether an eye is open, closed, or in between. By analyzing surrounding frames, and possibly the video as a whole, a blink can be differentiated from a wink, sleeping or relaxing, looking down, and the like. The analyzing can comprise determining a classifier 121 for a blink in order to identify eye blinks in the video. In some embodiments, the blink event is detected using the classifier. The flow 100 includes using the blink event and one or more other blink events to determine blink-rate information 130. The analyzing can filter out single eye winks 122 as eye winks sometimes represent a conscious act and may not be a reliable indicator of mental state. The analyzing can filter out looking down 123 by the individual. As the individual looks down, the individual's eyes can give an appearance of blinking, depending on the position of the camera, even if the eyes do not actually blink. Likewise eye closures, which are longer than blinks, can be filtered. In at least some embodiments, the classifier is configured to do the filtering and differentiation for winks, looking down, and eye closures.

The video is analyzed for information in addition to eye blink-rate information in some embodiments. For example, the flow 100 can further comprise evaluating blink duration 124 because the length of time that an individual's eyes are closed can be indicative of one or more mental states. Some embodiments further comprise evaluating average blink duration 124. The blink-rate information can include information on blink duration. Some embodiments further comprise determining context for the individual. Some embodiments determine context directly from the video, such as lighting conditions, number of people in the room, or other context. Additional context can be gathered from other sources such as direct input by the user, login credentials, the programs currently running, file names being accessed, various types of sensors such as thermometers, or the computer's clock/calendar, among other inputs. Some embodiments include compensating blink-rate information for a context 126. For example, the brightness of the monitor or room can have an impact on the blink-rate that is unrelated to the individual's mental state, and therefore can be compensated for in order that the eye blink-rate may more accurately reflect the mental state of the individual.

The flow 100 further comprises inferring mental states of the individual based on the eye blink-rate information 140. The inferring can be based on the blink duration. The inferring of mental states can include one or more of attention, concentration, boredom, or fatigue. In some embodiments, the inferring of mental states includes one or more mental states of frustration, confusion, disappointment, hesitation, cognitive overload, focusing, engagement, exploration, confidence, trust, delight, disgust, skepticism, doubt, satisfaction, excitement, laughter, calmness, stress, sadness, anger, happiness, and curiosity. While various values of eye blink-rates and/or durations, as well as changes in the eye blink-rates and/or durations, can be indicative of various mental states, a higher blink rate can indicate a mental state of being focused. In some embodiments, the inferring can include evaluation of an impaired state, such as being ill or under the influence of alcohol or drugs. Various steps in the flow 100 may be changed in order, repeated, omitted, or the like without departing from the disclosed concepts. Various embodiments of the flow 100 may be included in a computer program product embodied in a non-transitory computer readable medium that includes code executable by one or more processors.

Figure 2:
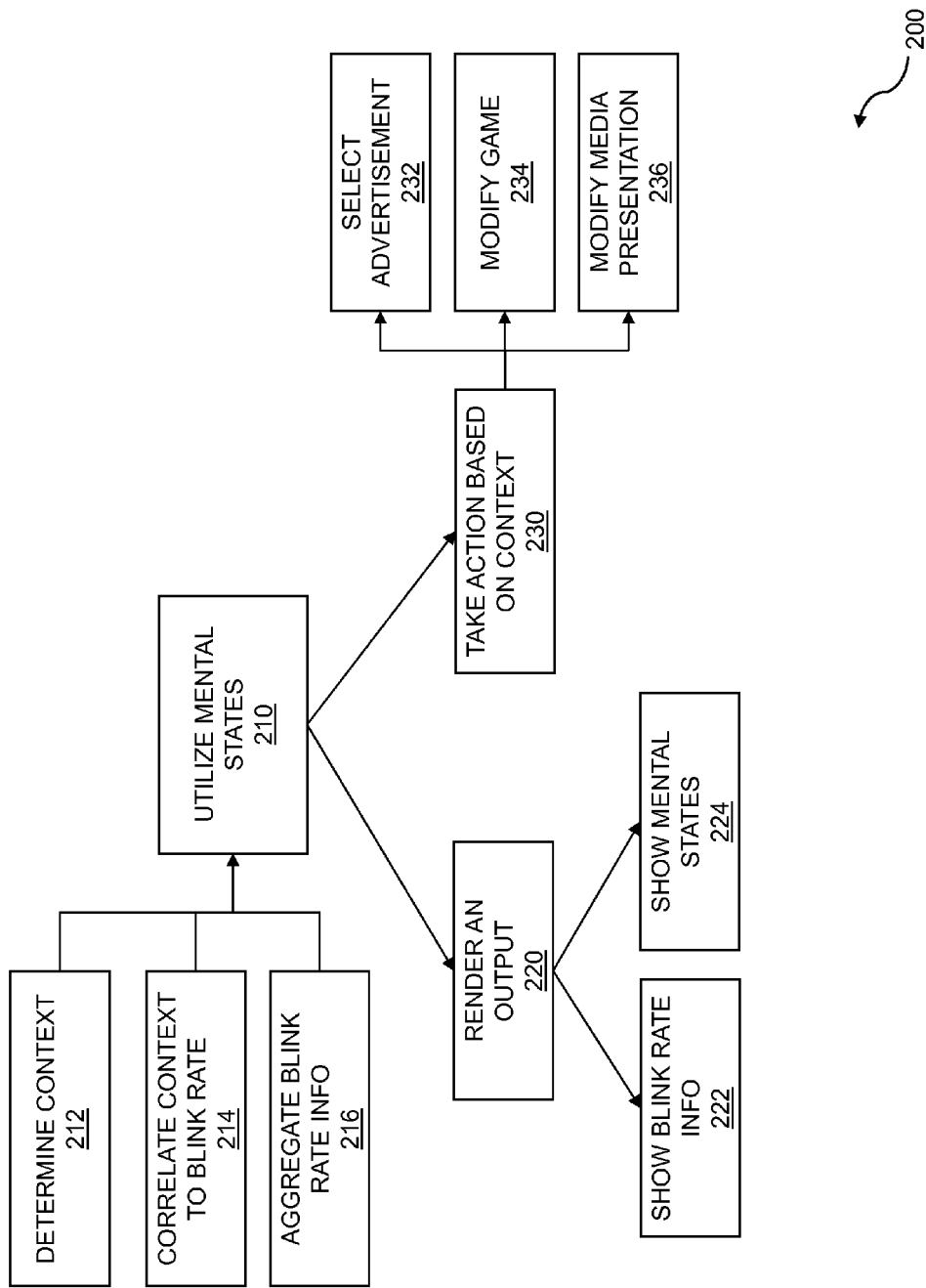
FIG. 2 is a flow diagram for mental state usage.

FIG. 2 is a flow diagram for mental state usage. A flow 200 can continue from or be part of the previous flow 100. The flow 200 includes utilizing mental state information 210 for one or more purposes. Some embodiments determine context 212 for use in conjunction with the mental state information. The context can include one or more of screen brightness, environmental brightness, gender, and demographics. In some embodiments, the context includes information about the task being performed, the media being presented, or the game being played. The context can vary over time. In some embodiments, the flow 200 can include correlating the context to the eye blink-rate information 214 to allow relationships between the contexts, the blink-rate information, and/or other mental state information to be determined. Thus the blink-rate information may be correlated with activities performed by the individual. In some embodiments, the flow 200 comprises aggregating the blink-rate information 216 for the individual with blink-rate information for a plurality of other people.

Some embodiments use the mental state information to render an output 220. The output can include the eye blink-rate information 222 and/or the mental states 224 which were inferred. The output display correlation between the blink-rate information and a stimulus which the individual is encountering. The mental states, which were inferred, can be correlated to a context for the individual. In some embodiments the mental states and/or the context trigger an action to be taken 230. The actions which may be taken based on inferred mental state include selecting an advertisement 232, modifying a game 234, modifying a media presentation 236, or the like. Various steps in the flow 200 may be changed in order, repeated, omitted, or the like without departing from the disclosed concepts. Various embodiments of the flow 200 may be included in a computer program product embodied in a non-transitory computer readable medium that includes code executable by one or more processors.

Figure 3:
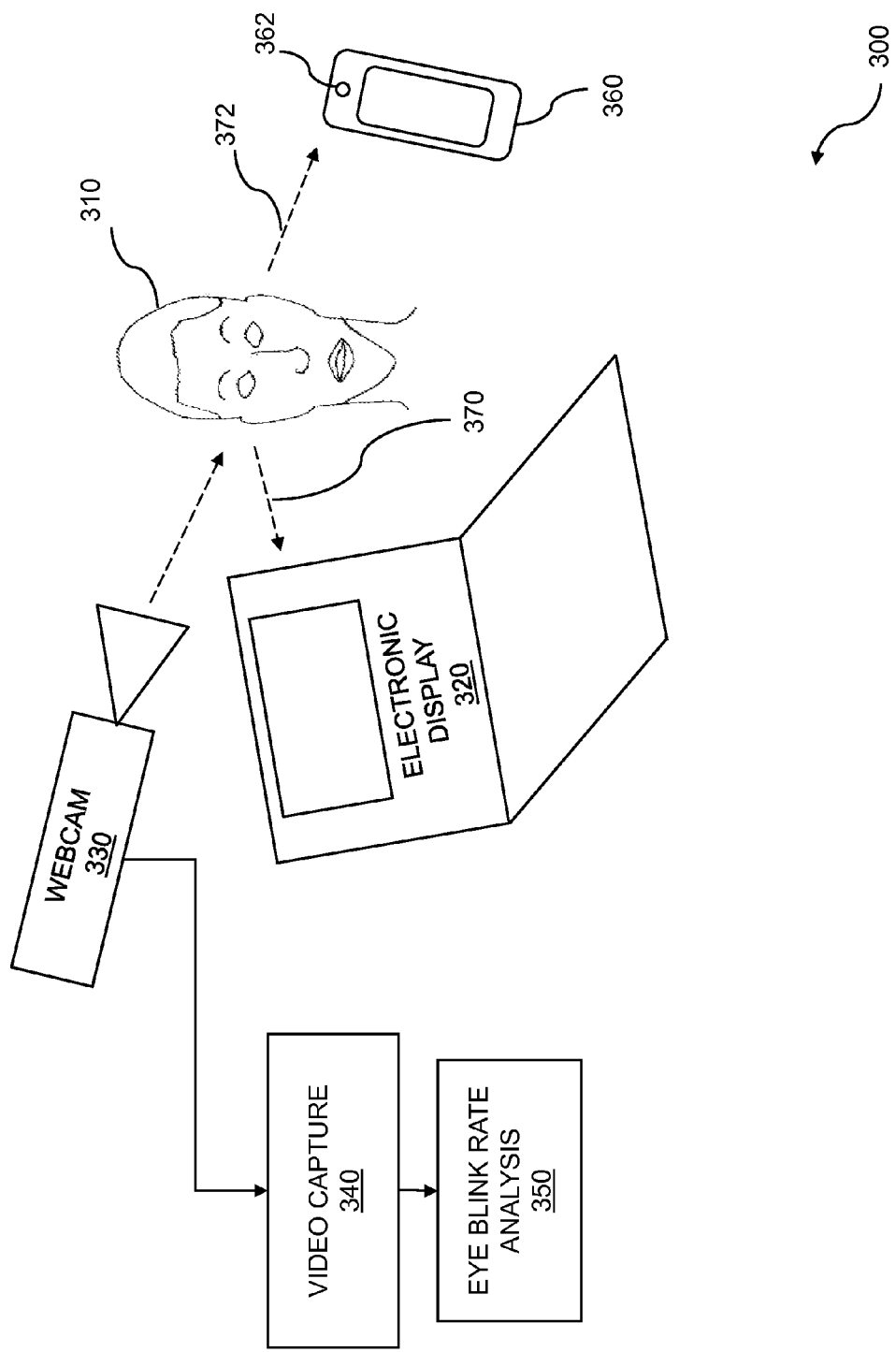
FIG. 3 is an image collection system for facial analysis.

FIG. 3 is an image collection system for facial analysis 300. An individual 310 can view 370 an electronic display 320 and mental state data (such as eye blink-rate information) on the individual 310 can be collected and analyzed. The electronic display 320 can show an output of a computer application that the individual 310 is using, or the electronic display 320 can show a media presentation so that the individual 310 is exposed to the media presentation. The display 320 can be any electronic display, including but not limited to, a computer display, a laptop screen, a net-book screen, a tablet screen, a cell phone display, a mobile device display, a remote with a display, a television, a projector, or the like. Likewise, other electronic displays can be viewed 372 such as a mobile device showing the media presentation and so on. The media presentation can include one of a group consisting of a movie, a television show, a web series, a webisode, a video, a video clip, an electronic game, an e-book, or an e-magazine. The electronic display 320 can be a part of, or may be driven from, the device collecting the mental state data, or the electronic display might only be loosely coupled with, or even unrelated to, the device collecting the mental state data, depending on the embodiment. The collecting can be accomplished with a mobile device 360 such as a cell phone, a tablet computer, or a laptop computer, and the mobile device can include a forward facing camera 362. The facial data can be collected with a camera such as the forward facing camera 362 of the mobile device 360 and/or by a webcam 330. Thus, the video can be obtained using a webcam 330. The video can be obtained from multiple sources, and in some embodiments, at least one of the multiple sources is a mobile device. The eye blink-rate information can be collected intermittently when the individual 310 is looking in the direction of a camera such as the front facing mobile camera 362 or the webcam 330. The camera can also capture images of the setting that can be used in determining contextual information.

The webcam 330 can capture video, audio, and/or still images of the individual 310. A webcam, as the term is used herein, can include a video camera, a still camera, a thermal imager, a CCD device, a phone camera, a three-dimensional camera, a depth camera, multiple webcams used to show different views of a person, or any other type of image capture apparatus that can allow captured data to be used in an electronic system. The images of the person 310 from the webcam 330 can be captured by a video capture unit 340. In some embodiments, video is captured, while in others, one or more still images are captured. The system 300 can include analyzing the video for eye blink-rate information 350, eye blink duration, facial data, and/or physiological data. The facial data includes information on facial expressions, action units, head gestures, smiles, smirks, brow furrows, squints, lowered eyebrows, raised eyebrows, or attention, in various embodiments. Analysis of physiological data can also be performed based on the video. Respiration, heart rate, heart rate variability, perspiration, temperature, and other physiological indicators of mental state can be determined by analyzing the video.

Figure 4:
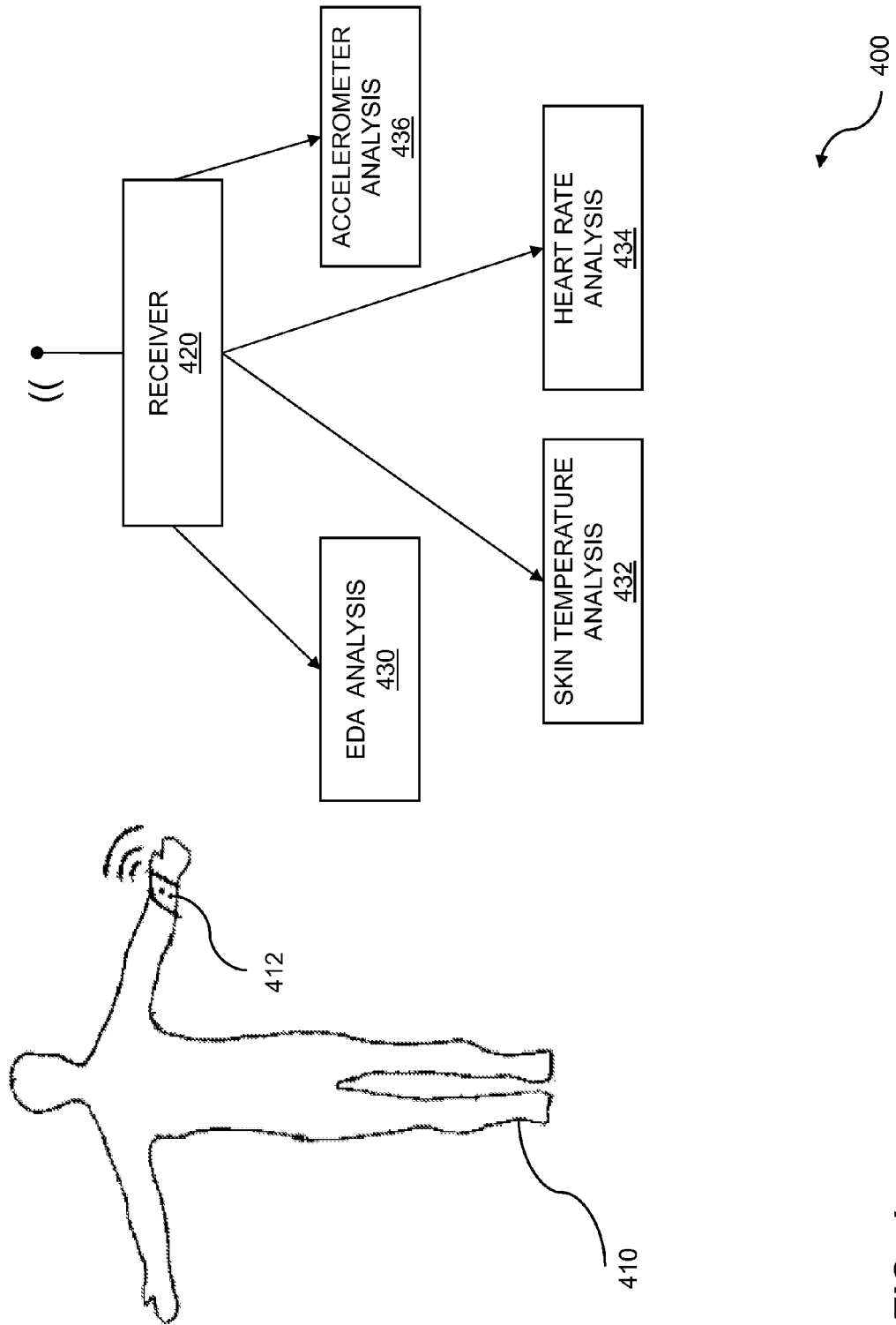
FIG. 4 is a diagram for sensor analysis.

FIG. 4 is a diagram for sensor analysis which can be used to assist or augment mental state analysis based on blink-rate information. A system 400 can analyze data collected from a person 410 as he or she interacts with a computer. The person 410 can have a biosensor 412 attached to him or her for the purpose of collecting mental state data. The biosensor 412 can be placed on the wrist, palm, hand, head, or other part of the body. In some embodiments, multiple biosensors are placed on the body in multiple locations. The biosensor 412 can include detectors for physiological data, which can include one or more of heart rate, heart rate variability, blink rate, skin temperature, and respiration. The biosensor 412 can transmit collected information to a receiver 420 using wireless technology such as Wi-Fi, Bluetooth, 802.11, cellular, or another band. In other embodiments, the biosensor 412 communicates with the receiver 420 by other methods, such as a wired or optical interface. The receiver can provide the data to one or more components in the system 400. In some embodiments, the biosensor 412 records multiple types of physiological information in memory for later download and analysis. In some embodiments, the download of recorded physiological data is accomplished through a USB port or another wired or wireless connection.

A process for mental state analysis can comprise collecting physiological data or accelerometer data with a biosensor. Mental states can be inferred based on physiological data (such as the physiological data captured by the sensor 412) along with blink-rate information. Mental states can also be inferred based, in part, on facial expressions and head gestures observed by a webcam or a combination of data from the webcam along with data from the sensor 412. The mental states can be analyzed based on arousal and valence. Arousal can range from being highly activated, such as when someone is agitated, to being entirely passive, such as when someone is bored. Valence can range from being very positive, such as when someone is happy, to being very negative, such as when someone is angry. Physiological data can include one or more of electrodermal activity (EDA), heart rate, heart rate variability, skin temperature, respiration, skin conductance or galvanic skin response (GSR), accelerometer readings, and other types of analysis of a human being. It will be understood that both here and elsewhere in this document, physiological information can be obtained either by biosensor 412 or by facial observation via the webcam 330.

Electrodermal activity can also be collected. The electrodermal activity can be analyzed 430 to indicate arousal, excitement, boredom, or other mental states based on observed changes in skin conductance. Skin temperature can also be collected and/or recorded on a periodic basis and in turn may be analyzed 432. Changes in skin temperature can indicate arousal, excitement, boredom, or other mental states. Heart rate information can be collected and recorded and can also be analyzed 434. A high heart rate can indicate excitement, arousal or another mental state. Accelerometer data can be collected and used to track one, two, or three dimensions of motion. The accelerometer data can be recorded. The accelerometer data can be used to create an actigraph showing an individual's activity level over time. The accelerometer data can be analyzed 436 and can indicate a sleep pattern, a state of high activity, a state of lethargy, or another state. The various data collected by the biosensor 412 can be used along with the eye blink-rate information captured by the webcam in the analysis of mental state. Contextual information can also be based on one or more of skin temperature or accelerometer data.

Figure 5:
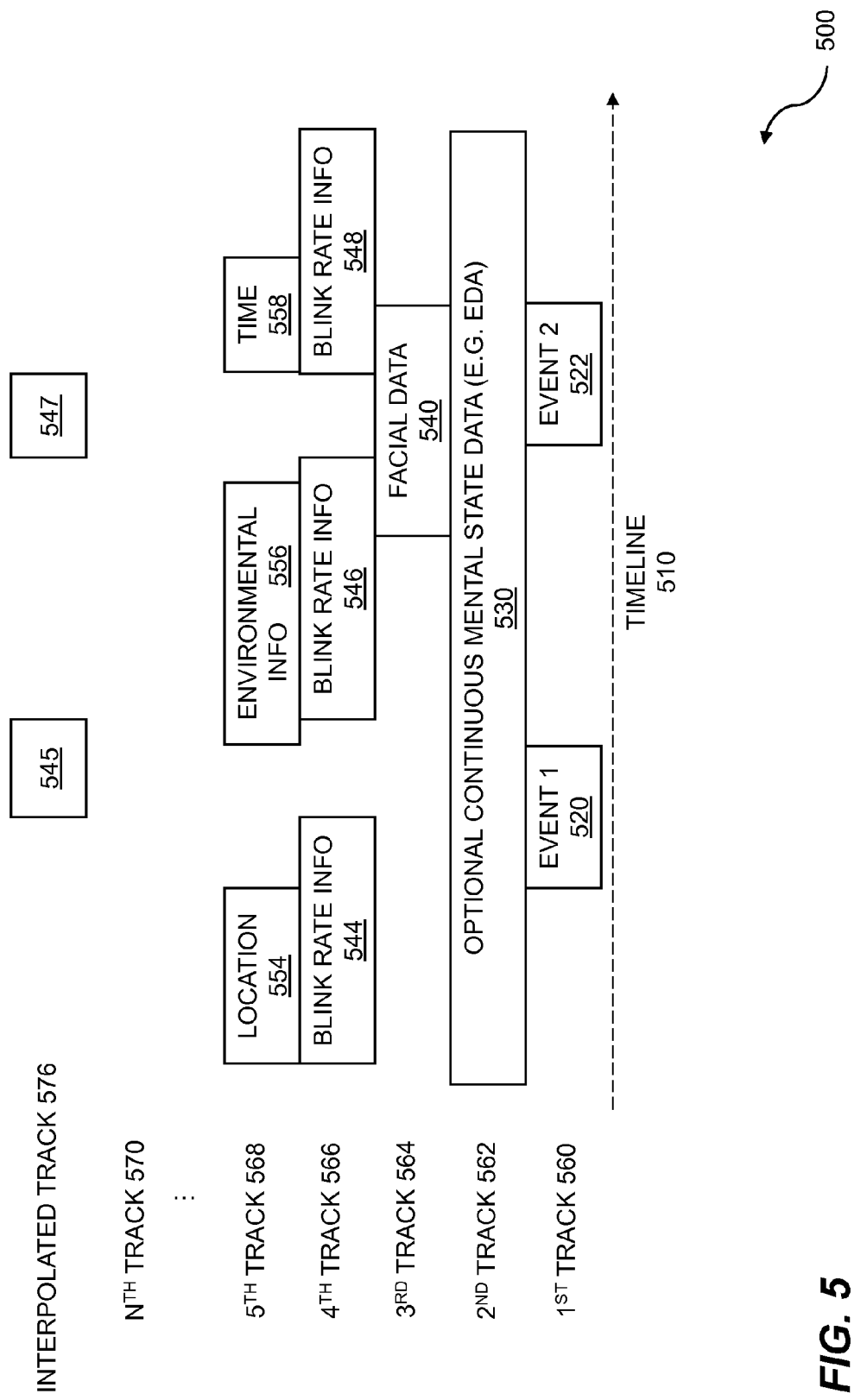
FIG. 5 is a timeline with information tracks relating to mental states.

FIG. 5 is a timeline 510 with information tracks 500 relating to mental states. The timeline can allow various data to be correlated, such as blink-rate information and contextual information. A first track 560 shows events that can be related to the individual's use of a computer. A first event 520 marker on the timeline can indicate an action that the individual took (such as launching an application); an action initiated by the computer (such as the presentation of a dialog box); an external event (such as a new global positioning system [GPS] coordinate); receiving an e-mail, phone call, or text message; or any other type of event. In some embodiments, a photograph is used to document an event or simply save contextual information in the first track 560. A second event 522 marker can indicate another action or event. Such event markers can be used to provide contextual information and may include data about emails, text messages, phone logs, file names, or any other information that can be useful in understanding the context of a user's actions.

A second track 562 can include continuously collected mental state data such as electrodermal activity data 530. A third track 564 can include mental state data such as facial data 540, which can be collected on an intermittent basis by a first camera (although in some embodiments the facial data is collected continuously). The facial data can be collected intermittently when the individual is looking toward a camera. The facial data 540 can include one or more still photographs, videos, or abstracted facial expressions, which can be collected when the user looks in the direction of the camera.

A fourth track 566 can include eye blink-rate information which can be determined using video. The video is collected sporadically, in some embodiments, so the blink-rate information may not be continuous. A first set of blink-rate information 544 can be determined for a first period of time, a second set of blink-rate information 546 can be determined for a second period of time, and a third set of blink-rate information 548 can be determined for a third period of time.

A fifth track 568 can include contextual data, which is collected along with the collection of the mental state data. In the example shown, the fifth track 568 includes location 554, environmental information 556, and time 558, although other types of contextual data can be collected in other embodiments. In the embodiment shown, the fifth track 568 allows contextual data to be associated with, and correlated to, the fourth track 566 containing the eye blink-rate information. Some analysis can evaluate and combine multiple tracks of additional data associated with one or more tracks of mental state data. For example, another track can include identity information about the individual being monitored by a camera, in embodiments, the same camera that captures the third track 564 or the fourth track 566 of mental state data.

Additional tracks, through the nth track 570, of mental state data or additional data of any type can be collected. The additional tracks 570 can be collected on a continuous or on an intermittent basis. The intermittent basis can be either occasional or periodic. Analysis can further comprise interpolating mental state data when the mental state data collected is intermittent, and/or imputing additional mental state data where the mental state data is missing. One or more interpolated tracks 576 can be included and can be associated with mental state data that can be collected on an intermittent basis, such as the eye blink-rate data of the fourth track 566. Interpolated data 545 and a second instance of interpolated data 547 can contain interpolations of the eye blink-rate data of the fourth track 566 for the time periods where no blink-rate data was collected in that track. Other embodiments can interpolate data for periods where other types of information are missing. In other embodiments, analysis includes interpolating mental state analysis when the collected mental state data is intermittently available.

Figure 6:
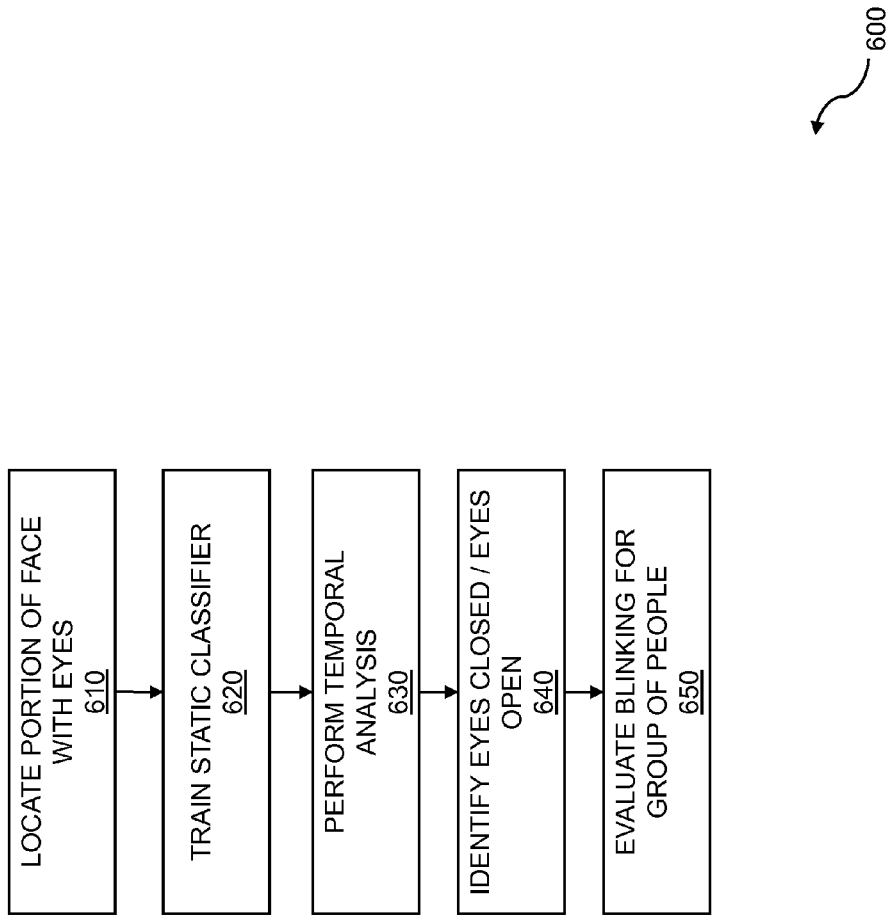
FIG. 6 is a flow diagram for blink analysis.

FIG. 6 is a flow diagram for blink analysis. A flow 600 can continue from or be part of the previous flow 100 or flow 200, or flow 600 may be performed independently of flow 100 to provide additional data analysis. The flow 600 can be used to aid in blink event determination and includes locating a portion of a face with eyes 610. The boundaries of the eyes, eyelids, and other portions of the face can be used to identify the needed portion. In embodiments, the flow 600 includes training a static classifier 620 to aid in the determination of when the eyes blink. The classifier can be trained off line using numerous images or videos. The classifier can be downloaded from a database for use in the blink analysis. The static classifier can identify when there are open eyes. The static classifier can identify when there are closed eyes. The flow 600 includes performing temporal analysis 630 on the portion of the face. Frame-by-frame analysis can be performed. In embodiments, 30 frames per second are obtained from the video. In most cases, a blink involves eyes closing for a single frame of a video. The flow 600 includes identifying that the eyes are closed 640 for a frame of the video using the temporal analysis.

In embodiments, the flow 600 includes evaluating blinking for a group of people 650 of which the individual is a part. If a group of people are simultaneously viewing an event, a video, or another media presentation, then the group of people will often blink at the same time. The blinking can occur at a scene change, a lighting change, and so on. If someone is not paying attention, then the person's blinking can occur at different times from those who are paying attention. The method can include evaluating synchronicity of blinking for the group. In some embodiments, the method includes determining a difference in blinking between the individual and a remainder of the group. The difference can be used to determine a mental state for the individual. In some cases the mental state includes lacking attention. Various steps in the flow 600 may be changed in order, repeated, omitted, or the like without departing from the disclosed concepts. Various embodiments of the flow 600 may be included in a computer program product embodied in a non-transitory computer readable medium that includes code executable by one or more processors.

Figure 7:
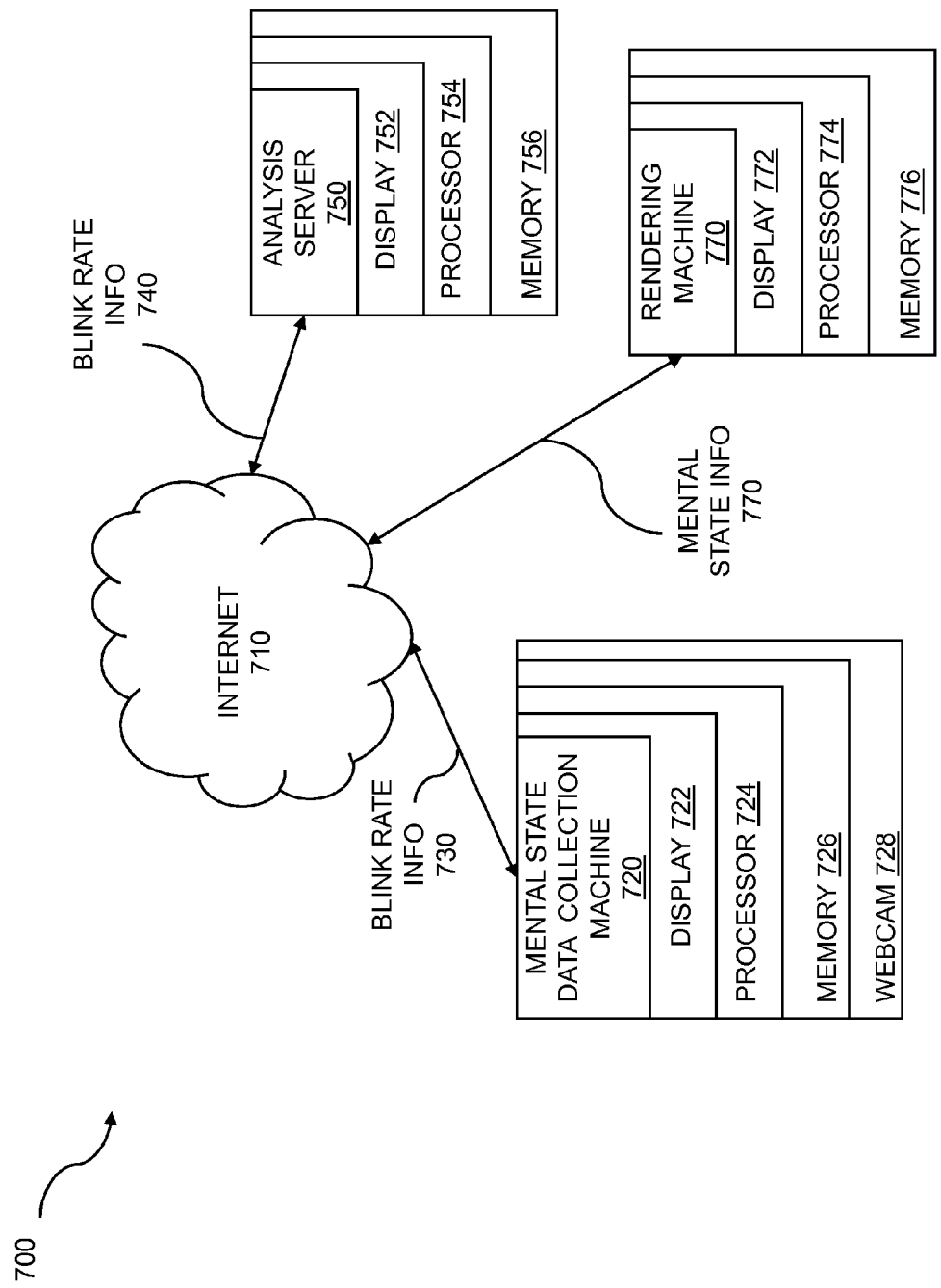
FIG. 7 is a system diagram for mental state analysis.

FIG. 7 is a system diagram for mental state analysis based on eye blink-rate information. The system 700 can include one or more computers coupled together by a communication link such as the Internet 710. The system 700 can also include a mental state collection machine 720, which can also be referred to as a client machine. The mental state collection machine 720 includes a memory 726 which stores instructions, one or more processors 724 coupled to the memory, a display 722, and a webcam 728. The memory 724 can be used for storing instructions, mental state data, blink-rate information, media presentations, and so on. The display 722 can be any electronic display, including but not limited to, a computer display, a laptop screen, a net-book screen, a tablet screen, a cell phone display, a mobile device display, a remote with a display, a television, a projector, or the like. The webcam 728, as the term is used herein, can refer to a camera on a computer (such as a laptop, a net-book, a tablet, or the like), a video camera, a still camera, a cell phone camera, a mobile device camera (including, but not limited to, a forward facing camera), a thermal imager, a CCD device, a three-dimensional camera, a depth camera, multiple webcams used to capture different views of viewers, or any other type of image capture apparatus that allows image data to be captured and used by an electronic system.

An individual can interact with the mental state collection machine 720, interact with another computer, or view a media presentation on another electronic display, among other activities. The mental state collection machine 720 can capture video of the interacting individual, and determine blink-rate information for the individual based on the video. The mental state collection machine 720 can then infer mental states based on the blink-rate information or in some way process mental state data that was collected. The mental state collection machine 720 can then send the blink-rate information 730 to another computer (such as the analysis server 750) across the internet 710 or using another computer-aided communications medium. In some embodiments, the mental state collection machine 720 sends the raw video showing a blinking individual to another machine. In other embodiments, the mental state collection machine infers mental states and sends the mental states to another machine, such as the rendering machine 770. In some embodiments, the one or more processors 724 can be configured to perform a computer-implemented method for mental state analysis comprising capturing video of an individual, analyzing the video to determine eye blink-rate information, and sending the eye blink-rate information.

Some embodiments can include an analysis server 750. The analysis server 750 can include one or more processors 754 coupled to a memory 756 to store instructions. In embodiments, the analysis server 750 includes a display 752. The analysis server 750 can receive the blink rate information 740 from the mental state collection machine 720 through the internet 710. The one or more processors 754 can be configured to perform a computer-implemented method for mental state analysis, which, in embodiments, comprises receiving eye blink-rate information obtained from video of an individual and inferring mental states of the individual based on the eye blink-rate information. In some embodiments, the analysis server 750 is configured as a web server, so the inferring of the mental states can be performed by a web service.

The system 700 can include a rendering machine 770. The rendering machine can include one or more processors 774 coupled to a memory 776 to store instructions and a display 772. The rendering machine 770 can receive the mental state information 770 from the Internet 710 or another computer-aided communication method. The mental state information 770 can include eye blink-rate information from the analysis server 750 or from the mental state data collection machine 720, and can render an output to the display 772. So, the system 700 can enable a computer-implemented method for mental state analysis comprising receiving eye blink-rate information based on video of an individual, receiving mental state information inferred from the eye blink-rate information, and rendering one or more of the eye blink-rate information and the mental state information which was inferred. The system 700 can comprise a computer program product embodied in a non-transitory computer readable medium for mental state analysis including code for obtaining video of an individual, code for analyzing the video to determine eye blink-rate information, and code for inferring mental states of the individual based on the eye blink-rate information.

Each of the above methods may be executed on one or more processors on one or more computer systems. Embodiments may include various forms of distributed computing, client/server computing, and cloud-based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams, show functions, steps, or groups of steps of the methods, apparatus, systems, computer program products and/or computer-implemented methods. Any and all such functions—generally referred to herein as a "circuit," "module," or "system"—may be implemented by computer program instructions, by special-purpose hardware-based computer systems, by combinations of special purpose hardware and computer instructions, by combinations of general purpose hardware and computer instructions, and so on.

A programmable apparatus which executes any of the above mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are neither limited to conventional computer applications nor the programmable apparatus that run them. To illustrate: the embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the causal entity.

While the invention has been disclosed in connection with preferred embodiments shown and described in detail, various modifications and improvements thereon will become apparent to those skilled in the art. Accordingly, the forgoing examples should not limit the spirit and scope of the present invention; rather it should be understood in the broadest sense allowable by law.

What is claimed is:

1. A computer-implemented method for mental state analysis comprising:
    obtaining video of an individual;
    analyzing, using one or more processors, the video to detect a blink event based on a classifier for a blink that was determined wherein the blink event is determined by:
    locating a portion of a face with eyes;
    performing temporal analysis on the portion of the face; and
    identifying that the eyes are closed for a frame in the video using the temporal analysis;
    evaluating a blink duration of the individual for the blink event;

determining blink-rate information using the blink event and one or more other blink events;
compensating the blink-rate information for a context;
evaluating blinking for a group of people of which the individual is a part;
evaluating an average blink duration for the group of people;
determining a difference in blinking between the individual and a remainder of the group; and
inferring mental states of the individual for the blink event, wherein the mental states are based on the blink event, the blink duration of the individual, the average blink duration for the group of people, and the blink-rate information that was compensated.

2. The method of claim 1 wherein the analyzing filters out single eye winks.

3. The method of claim 1 wherein the analyzing filters out looking down by the individual.

4. The method of claim 1 wherein the context includes one or more of screen brightness, environment brightness, gender, and demographics.

5. The method of claim 1 further comprising aggregating the blink-rate information for the individual with blink-rate information for a plurality of other people.

6. The method of claim 1 further comprising correlating the blink-rate information with activities performed by the individual.

7. The method of claim 1 wherein the blink-rate information is correlated to a stimulus that the individual is encountering.

8. The method of claim 1 further comprising determining the classifier for a blink.

9. The method of claim 1 wherein the video is obtained from multiple sources.

10. The method of claim 9 wherein at least one of the multiple sources is a mobile device.

11. The method of claim 1 wherein the video is collected sporadically.

12. The method of claim 1 further comprising determining context for the individual.

13. The method of claim 1 wherein the inferring is performed by a web service.

14. The method of claim 1 wherein the inferring of mental states includes one or more of attention, concentration, boredom, or fatigue.

15. The method of claim 1 wherein the inferring of mental states includes one or more mental states of frustration, confusion, disappointment, hesitation, cognitive overload, focusing, engagement, exploration, confidence, trust, delight, disgust, skepticism, doubt, satisfaction, excitement, laughter, calmness, stress, anger, happiness, and curiosity.

16. The method of claim 1 wherein a higher blink rate indicates a mental state of being focused.

17. The method of claim 1 wherein the inferring includes evaluation of an impaired state.

18. The method of claim 1 further comprising analyzing the video for facial data or physiological data.

19. The method of claim 18 wherein the physiological data includes one or more of heart rate, heart rate variability, blink rate, skin temperature, and respiration.

20. The method of claim 1 further comprising collecting physiological data or accelerometer data with a biosensor.

21. The method of claim 20 wherein the physiological data includes one or more of heart rate, heart rate variability, electrodermal activity, skin temperature, and respiration.

22. The method of claim 1 further comprising correlating the mental states, which were inferred, to a context for the individual.

23. The method of claim 1 wherein the mental states, which were inferred, are used for advertisement selection.

24. The method of claim 1 wherein the mental states, which were inferred, are used to modify a game.

25. The method of claim 1 wherein the mental states, which were inferred, are used to modify a media presentation.

26. A computer program product embodied in a non-transitory computer readable medium for mental state analysis, the computer program product comprising code which causes one or more processors to perform operations of:
obtaining video of an individual;
analyzing the video to determine a blink event based on a classifier for a blink that was determined wherein the blink event is determined by:
locating a portion of a face with eyes;
performing temporal analysis on the portion of the face; and
identifying that the eyes are closed for a frame in the video using the temporal analysis;
evaluating a blink duration of the individual for the blink event;
determining blink-rate information using the blink event and one or more other blink events;
compensating the blink-rate information for a context;
evaluating blinking for a group of people of which the individual is a part;
evaluating an average blink duration for the group of people;
determining a difference in blinking between the individual and a remainder of the group; and
inferring mental states of the individual for the blink event, wherein the mental states are based on the blink event, the blink duration of the individual, the average blink duration for the group of people, and the blink-rate information that was compensated.

27. A computer system for mental state analysis comprising:
a memory which stores instructions;
one or more processors attached to the memory wherein the one or more processors, when executing the instructions which are stored, are configured to:
obtain video of an individual;
analyze the video to determine a blink event based on a classifier for a blink that was determined wherein the blink event is determined by:
locating a portion of a face with eyes;
performing temporal analysis on the portion of the face; and
identifying that the eyes are closed for a frame in the video using the temporal analysis;
evaluate a blink duration of the individual for the blink event;
determine blink-rate information using the blink event and one or more other blink events;
compensate the blink-rate information for a context;
evaluate blinking for a group of people of which the individual is a part;
evaluate an average blink duration for the group of people;
determine a difference in blinking between the individual and a remainder of the group; and
infer mental states of the individual for the blink event, wherein the mental states are based on the blink event, the blink duration of the individual, the average blink duration for the group of people, and the blink-rate information that was compensated.

28. The method of claim 1 further comprising training a static classifier to determine when the eyes blink.

29. The method of claim 28 wherein the static classifier identifies that the eyes are open.

30. The method of claim 28 wherein the static classifier identifies that the eyes are closed.

31. The method of claim 1 further comprising evaluating synchronicity of blinking for the group.

32. The method of claim 1 wherein the difference is used to determine a mental state for the individual.

33. The method of claim 32 wherein the mental state includes lacking attention.

34. The method of claim 1 wherein eye closures, which are longer than blinks, are filtered.

35. The method of claim 28 wherein the training is done offline using a plurality of images or videos.

36. The method of claim 28 wherein the classifier is further configured to do filtering and differentiation.

37. The method of claim 36 wherein the filtering and differentiation is for winks, looking down, or eye closures.

38. The method of claim 1 further comprising downloading the classifier from a database for use in the blink analysis.

* * * * *